United States Patent
McIntyre et al.

(10) Patent No.: US 11,723,641 B2
(45) Date of Patent: Aug. 15, 2023

(54) CAMERA SYSTEM FOR USE WITH RETRACTORS

(71) Applicant: Viseon, Inc., Irvine, CA (US)

(72) Inventors: Todd D. McIntyre, Irvine, CA (US); Anthony Pham, Irvine, CA (US); Ravut Chhit, Irvine, CA (US); Peter G. Davis, Irvine, CA (US)

(73) Assignee: Viseon, Inc., Irvine, CA (US)

( * ) Notice: Subject to any disclaimer, the term of this patent is extended or adjusted under 35 U.S.C. 154(b) by 81 days.

(21) Appl. No.: 17/444,328

(22) Filed: Aug. 3, 2021

(65) Prior Publication Data
US 2023/0045279 A1 Feb. 9, 2023

(51) Int. Cl.
*A61B 17/02* (2006.01)
*A61B 1/00* (2006.01)
*A61B 1/04* (2006.01)
*A61B 17/00* (2006.01)

(52) U.S. Cl.
CPC ...... *A61B 17/0218* (2013.01); *A61B 1/00194* (2022.02); *A61B 1/042* (2013.01); *A61B 2017/00477* (2013.01)

(58) Field of Classification Search
CPC ........ A61B 17/02–0206; A61B 17/025; A61B 2017/0256–0262; A61B 1/32
See application file for complete search history.

(56) References Cited

U.S. PATENT DOCUMENTS

| | | | |
|---|---|---|---|
| 2,675,462 A | 4/1954 | Newton | |
| 4,905,670 A * | 3/1990 | Adair | A61B 1/32 600/246 |
| 5,502,598 A | 3/1996 | Kimura et al. | |
| 5,813,978 A | 9/1998 | Jako | |
| 6,364,830 B1 | 4/2002 | Durell | |
| 9,492,065 B2 | 11/2016 | Tesar et al. | |
| 10,646,212 B2 | 5/2020 | Chhit et al. | |
| 11,166,706 B2 | 11/2021 | Charles et al. | |

(Continued)

FOREIGN PATENT DOCUMENTS

| CN | 109662741 | 4/2019 |
|---|---|---|
| EP | 3769658 | 1/2021 |

(Continued)

OTHER PUBLICATIONS

Combined Search and Examination Report dated Jan. 13, 2022 from GB Patent Application No. GB2117300.0.

(Continued)

*Primary Examiner* — Eduardo C Robert
*Assistant Examiner* — Michelle C Eckman
(74) *Attorney, Agent, or Firm* — Crockett & Crockett, PC; K. David Crockett, Esq.

(57) ABSTRACT

A camera system for use with retractors. The system includes a camera assembly configured for mounting on the proximal end of a retractor system, such as the proximal end of a blade such that the entirety of the camera assembly is disposed at the proximal end of the retractor system may be disposed such that the distal-most optical element overhangs the working channel established by the retractor, and includes a reflector and a rotatable mount for the reflector, camera assembly viewing axis may be altered without changing the position of the entire camera assembly.

25 Claims, 8 Drawing Sheets

(56) References Cited

U.S. PATENT DOCUMENTS

| | | |
|---|---|---|
| 2002/0058229 A1 | 5/2002 | Sugimoto |
| 2003/0055437 A1 | 3/2003 | Yasunaga |
| 2010/0274089 A1 | 10/2010 | Choi et al. |
| 2014/0005484 A1* | 1/2014 | Charles .................. A61B 34/20 600/201 |
| 2019/0307439 A1* | 10/2019 | Chhit ..................... A61B 1/042 |
| 2020/0261071 A1 | 8/2020 | Chhit et al. |
| 2021/0109340 A1 | 4/2021 | Liang et al. |

FOREIGN PATENT DOCUMENTS

| | | |
|---|---|---|
| GB | 2553045 | 2/2018 |
| KR | 1020150053630 | 5/2015 |
| WO | WO2015081008 | 6/2015 |
| WO | WO2019152523 | 8/2019 |
| WO | WO2020167418 | 8/2020 |

OTHER PUBLICATIONS

International Search Report and Written Opinion dated Nov. 18, 2022 from IA PCT/US2022/039201.
Examination Report No. 1 dated Sep. 27, 2022 from Australian Patent Application No. 2021273512.
Examination Report No. 2 dated Nov. 18, 2022 from Australian Patent Application No. 2021273512.
Notice of Acceptance dated Dec. 19, 2022 from Australian Patent Application No. 2021273512.
Notice of Grant dated Sep. 27, 2022 from Great Britain Patent Application No. 2117300.0.

* cited by examiner

Fig. 2
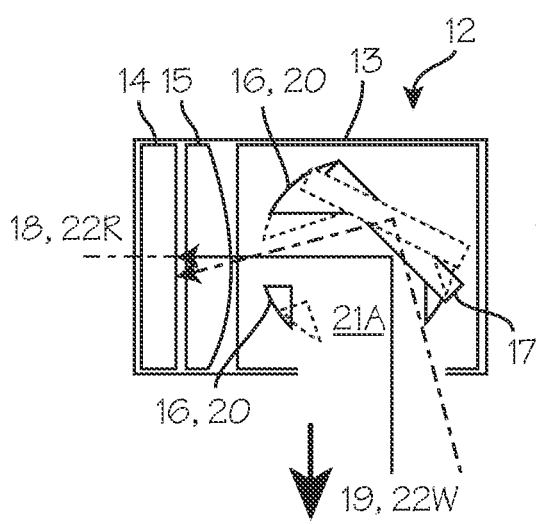
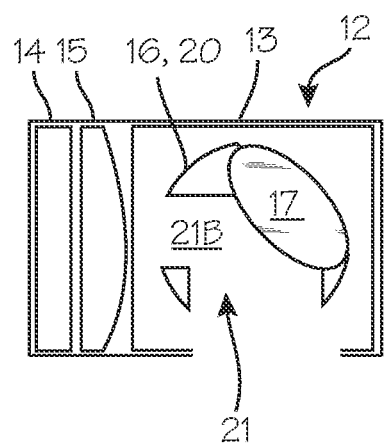
Fig. 3
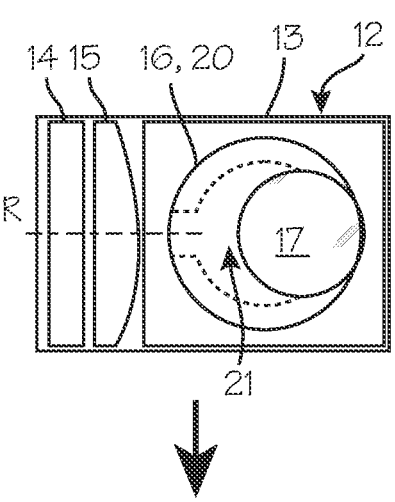
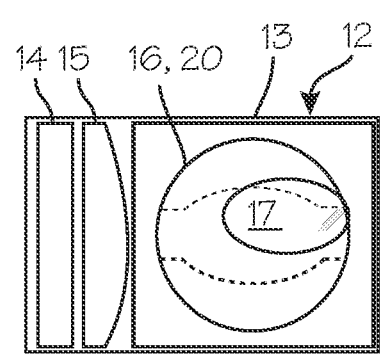

Fig. 11
Fig. 12
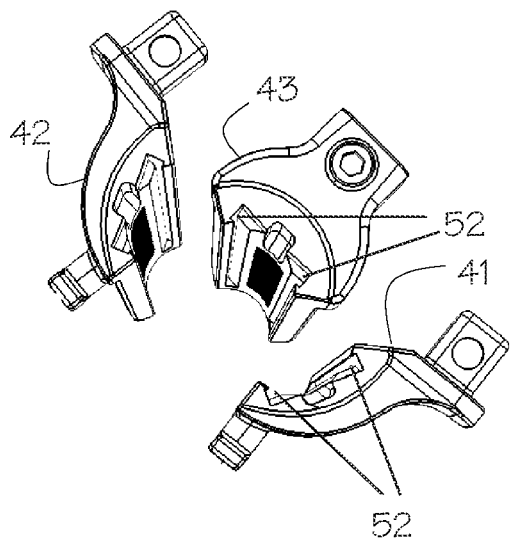
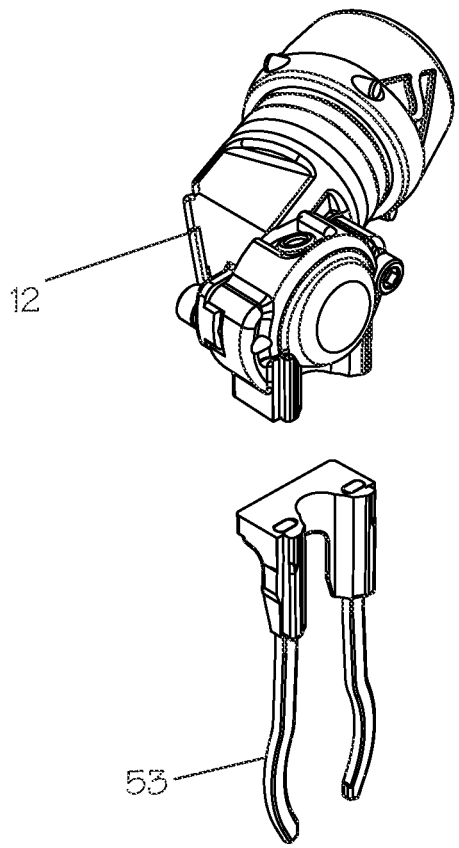

us 11,723,641 B2

CAMERA SYSTEM FOR USE WITH RETRACTORS

FIELD OF THE INVENTIONS

The inventions described below relate to the field of minimally invasive surgery.

BACKGROUND OF THE INVENTIONS

Retractors with cameras mounted on components of the retractors have been used for various surgeries, including spine surgery and abdominal surgery. Tesar, U.S. Pat. No. 9,492,065 (Nov. 15, 2016) discloses a retractor for abdominal surgery, with cameras mounted on the circular frame, or blades of the retractor. Chhit, U.S. Pub. 20200261071 (Aug. 20, 2020) discloses a retractor for spinal surgery, with camera assemblies mounted on a retractor frame or a retractor blade. In each of these systems, the entire camera assembly may be rotated relative to the retractor system to point the camera to different areas of a surgical field at the distal end of the retractor blades. The camera assembly, being rotatable relative to the retractor, is also subject to accidental impact and alteration of the viewing axis of the camera assembly as the surgeon passes surgical tools into and out of the working channel established by the retractor.

SUMMARY

The devices and methods described below provide for improved visualization of a surgical work space held open with a retractor. A camera assembly configured for mounting on the proximal end of a retractor system, such as the proximal end of a blade, a retractor frame, or the proximal rim of a cannula tube, and includes a distal-most optical surface which, in the preferred embodiment, is disposed at the proximal end of the cannula system such that the entirety of the camera assembly is disposed at the proximal end of the retractor system. The distal-most optical element in the camera assembly may be disposed at the proximal end of the retractor system, and may be disposed proximal to the proximal end of the retracting element (blade or cannula tube), and may be disposed such that the distal-most optical element overhangs the working channel established by the retractor.

BRIEF DESCRIPTION OF THE DRAWINGS

FIGS. 2, 3, 4, and 5 illustrate camera assemblies configured for adjustment of the viewing axis of the camera assembly.

FIGS. 9, 10 and 11 illustrate typical retractor with which the camera assembly of FIGS. 2, 3 and 7 may be used.

FIG. 12 illustrates a camera assemble with a mounting structure suited for use with the retractor blades of FIGS. 9, 10 and 11.

DETAILED DESCRIPTION OF THE INVENTIONS

Figure 1:
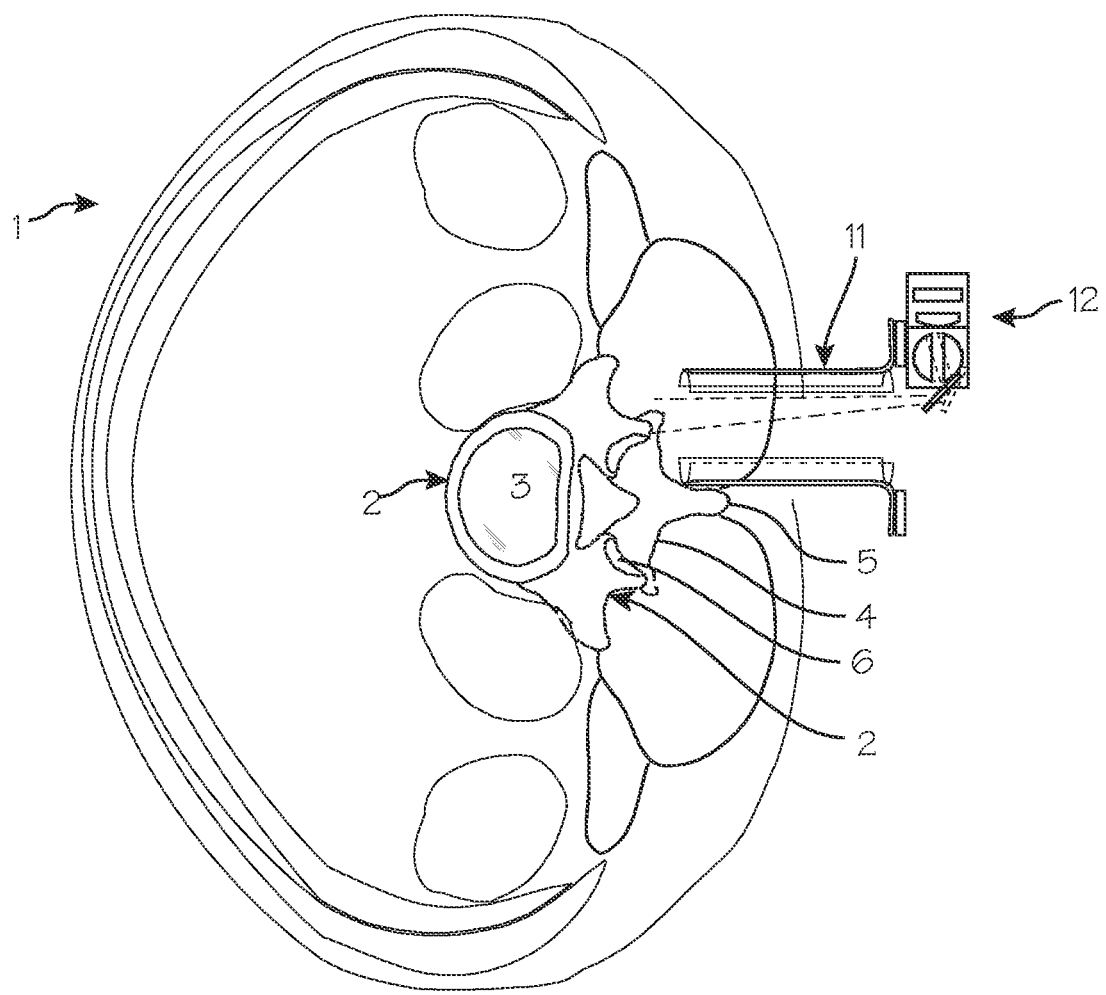
FIG. 1 is a coronal cross section of a patient illustrating a typical placement of a retractor system and camera assembly in which the rotatable mirror may be used to direct the viewing angle of the camera assembly to different areas of the surgical workspace at the distal end of the retractor blades.

FIG. 1 is a coronal cross section of a patient 1, taken through the midsection at the level of the lower back and lumbar spine, illustrating a typical placement of a retractor system and camera assembly in which the rotatable mirror may be used to direct the viewing angle of the camera assembly to different areas of the surgical workspace at the distal end of the retractor blades. The anatomy shown in FIG. 1 includes the vertebra 2, an intervertebral disc 3, lamina 4 and spinous process 5, and the articular joint 6 to an adjacent vertebra, each of which might need to be addressed surgically to treat a variety of conditions.

To gain access to any of these structures, a surgeon may approach the spine through a retractor system 11 placed in one of several pathways. For a laminotomy or laminectomy, for example, the retractor will be placed posteriorly to the spine, and inserted into an incision in the back. If the retractor is an expandable multi-blade retractor, the surgeon will separate the blades to create a large working channel. If the retractor is a cannula retractor or trocar, the lumen of the cannula will serve as the working channel. The working channel also serves as a viewing channel, such that the surgeon can view the surgical workspace through the same path used to insert tools into the surgical space.

To provide better viewing, the camera assembly 12 may be fixed to the proximal end of the retractor. The camera assembly may be fixed to a retractor blade of an expandable retractor or to the proximal end of a tube of a cannula retractor, or to the frame of a multi-blade retractor, or to the proximal end of a single blade retractor, or other retracting element. Especially for expandable retractors, the size of the working channel will change as the retractor is expanded and the blades move apart, so that it will be helpful to adjust the viewing axis of the camera assembly. Lighting, such as LED's, can be integrated into the retractor as desired to enhance imaging of the camera assembly.

FIGS. 2 and 3 illustrate a camera assembly configured for adjustment of the viewing axis of the camera assembly by rotating a reflector without rotation of the entire camera assembly, and without movement of the imaging sensor. As shown in FIG. 2, the camera assembly 12 comprises a housing 13 with an imaging sensor 14 disposed at a first end of the housing, a lens assembly 15, a rotatable reflector mount 16 and a reflector 17 mounted on the reflector mount at the second end of the housing. The rotatable reflector mount is disposed between the imaging sensor and the reflector, and is rotatably disposed within the housing such that it can tilt the mirror in planes intersecting the central viewing axis 18 of the imaging sensor (typically perpendicular to the flat face of the imaging sensor). The reflector mount, when comprising an element disposed between the reflector and imaging sensor, is optically transmissive, such that light beams from the surgical workspace and reflected by the mirror will pass through the reflector mount to the lens 15 and imaging sensor 14. The reflector establishes a central viewing axis 19 of the camera assembly, and the rotatable reflector mount provides a means for rotating the mirror and thereby altering the viewing axis relative to the imaging axis of the sensor to provide views of the surgical workspace at the distal end of the retractor blades or retractor tube, without need to rotate the entire camera assembly. The reflector may be the distal-most optical component, but may be covered with a lens or other optical component which serves as the distal-most optical component, and preferably is disposed, when the camera assembly is fixed to a retractor, at the proximal end of the working channel established by the retractor blades, or proximal to, and overhanging the working channel established by the retractor blades.

The rotatable reflector mount 16 of FIGS. 2 and 3 may be provided in the form shown, with a generally spherical body 20 (a ball head, for example), or a body comprising a portion of a sphere, with a bore 21 with a first segment 21A passing through the body along a line 22W between the workspace and the reflector and a second segment 21B passing through the body along the line 22R of light reflected by the reflector toward the image sensor (the reflector reflection axis). The bore segments establish optical apertures in the spherical body 20, including an aperture closest to the surgical workspace (an objective aperture) and an aperture closest in the optical pathway to the image sensor (an ocular aperture). The bores may be open, empty bores, or they may be filled with optically transmissive or transparent material. The spherical body may be truncated, as shown, to provide a flat surface at the objective aperture, and truncated to establish a flat surface along a cord set at an angle to the reflector reflection axis. In this geometry, the truncated flat surface along the cord corresponds to the flat plane of the reflector, and is set at a 45° angle to both the axis of the bore first segment 21A and the second bore segment 21B when the spherical body 20 is in a neutral position. This angle may be varied to accommodate retractors of various configuration, to avoid interference with other structures on the retractor. The reflector, or the aperture closest to the surgical workspace (an objective aperture) in the reflector mount/spherical body, or an optical element disposed with the aperture may be the distal-most optical element, or the optical element closest to the objective, and preferably is disposed proximal to the proximal end of the retractor elements, or the working channel defined by the retractor elements.

Figure 4:
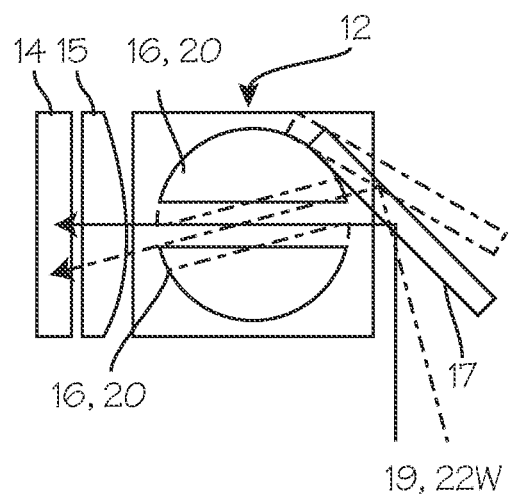
Figure 5:
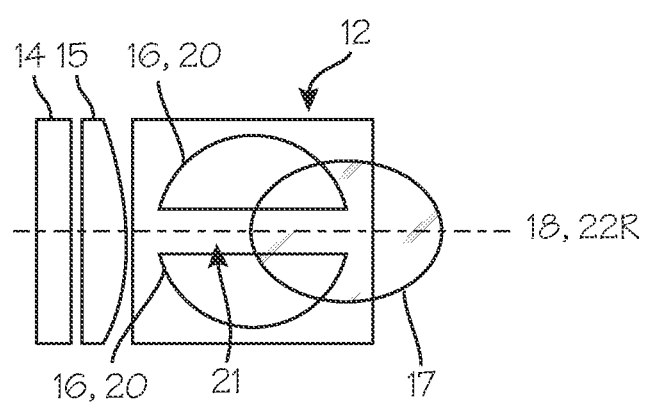

As shown in FIGS. 4 and 5, rotatable reflector mount 16 may be formed with a straight bore, passing straight through the rotatable reflector mount, and the reflector 17 may be disposed along the optical path to reflect light emanating from the work space, up through an aperture in the housing, to reflect light and images through the straight bore toward an area of the image sensor. The rotatable reflector mount 16 may comprise other means for rotating the mirror, such as gimbals or simple hinges, disposed within the housing such that mirror rotation can be achieved without rotating the entire camera assembly.

In the embodiments of FIGS. 2 through 5, the rotatable reflector mount is disposed between the imaging sensor and the reflecting element, with an optically transmissive portion of the rotatable reflector mount disposed between the imaging sensor and the reflecting element, and with the reflecting element fixed to the rotatable reflector mount. Where other forms of rotatable reflector mounts are used, such as gimbals or simple hinges, the rotatable reflector mount may be positioned elsewhere, and may be positioned with the reflector between the rotatable reflector mount and the imaging sensor.

The bore may be closed with an aperture fitting or lens to collimate the image to the sensor. The aperture fitting or lens may be fixed at the ocular end of the bore (the end closest to the image sensor) or the objective end of the bore (the end closest to the objective surgical field).

Figure 6:
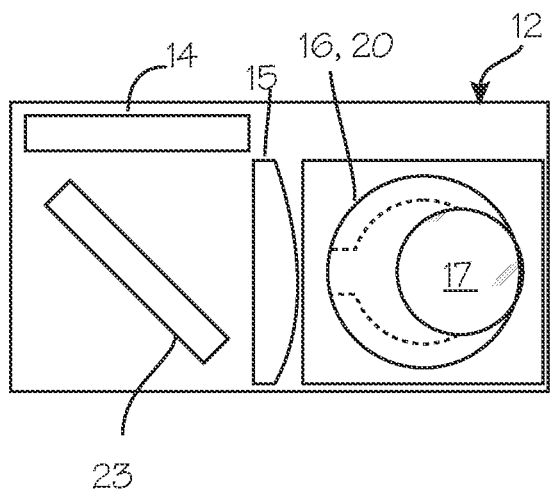
FIG. 6 illustrates a camera assembly configured for adjustment of the viewing axis of the camera assembly.

FIG. 6 illustrates an embodiment of the camera assembly with the rotatable reflector, rotatable reflector mount, lens and image sensor of the previous figures, illustrating use of additional reflector(s) 23 to redirect light and images from the first reflector 17, to permit placement of the imaging sensor offset from the reflection axis of the first reflector, in order to accommodate retractors which might have obstructive features close to otherwise suitable mounting features for the camera assembly. Additional reflectors may be used to align the imaging axis of the image sensor along an axis different from a bore axis or a reflector reflection axis, to collapse the optical pathway and minimize the size of the camera assembly and permit use of imaging sensor/lens combinations with various focal lengths. For example, additional reflector 23 directs light from the reflector 17 toward the image sensor which is not aligned with the reflector reflection axis, but is offset from the reflector reflection axis. A third reflector may be used to redirect light from the second reflector toward an imaging sensor with an imaging axis parallel to, but offset from the reflector viewing axis, and/or the central viewing axis 19 of the camera assembly. The second may be rotatably disposed relative to the first mirror, or the third mirror may be rotatably disposed relative to the second mirror, so allow more flexibility in placement of the imaging sensor and accommodate retractors of differing construction or different obstacles above the surgical field.

Figure 7:
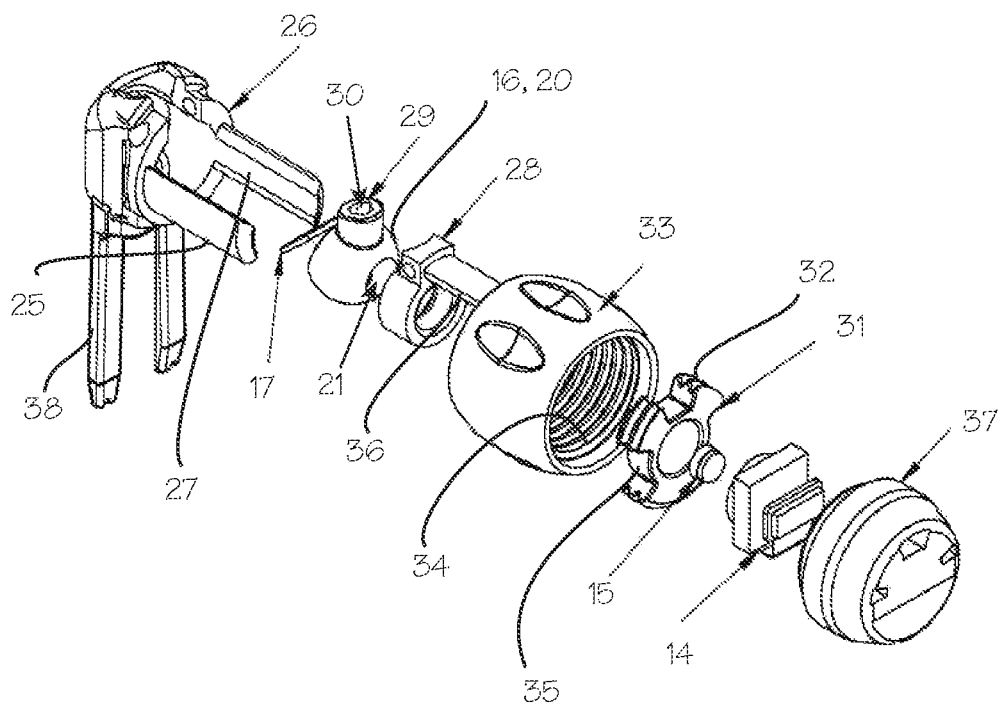
FIG. 7 is an exploded view of an embodiment of the camera assembly.

FIG. 7 illustrates an embodiment of the camera assembly, with various optional components which support the rotatable mirror. The reflector mount 16 may be provided in the form shown, with a generally spherical body 20 (a ball head, for example) with a bore 21. The spherical body 20 is mounted within the camera assembly in any manner allowing rotation in at least one plane (for example, restricted to tilting only in a plane established by the long axis of the retractor blade or tube), but preferably in any plane (to provide for panning left and right relative to the imaging sensor axis, or tilting up and down relative to the imaging sensor axis) which results in redirecting light and images emanating from the surgical workspace onto the imaging sensor 14.

The reflector mount 16 need not be spherical as shown, so long as it is rotatable with the camera housing to change the reflector viewing axis relative to the imaging sensor imaging axis. Though the bore 21 is a convenient way to provide optical transmissivity through the mount, a solid transparent (highly transmissive) spherical body may be used without the bore.

Additional components shown in FIG. 7 may be provided as convenient means for assembling the device and maintaining alignment of the mirror, mirror mount and imaging sensor while providing a convenient means for rotating the mirror and mounting the camera assembly on a retractor. As illustrated, the reflector mount spherical body 20 is captured between concave posts 25 provided in a front housing structure 26 and extending into the camera assembly. The posts have concave inner surfaces 27, with a concave contour matching the convex outer contour of the reflector mount spherical body 20. A reflector mount bearing ring 28 serves as a back stop to securely capture the reflector mount, to prevent translation of the reflector mount along the axis of the imaging sensor. A post 29 extends from the reflector mount spherical body 20 to provide a means for manipulating and rotating the reflector mount spherical body 20 within the housing and aim the mirror. The post 29 may extend from the housing so that it is directly manipulable by a surgeon, or it may be limited in height so that it is entirely disposed inside the boundaries of the housing (so that it may not be inadvertently moved) and provided with a socket 30 into which a surgeon may insert any suitable rod to manipulate and rotate the reflector mount spherical body 20. The post 29 is preferably disposed on the spherical body 20 such that it is upright when the spherical body 20 is in a neutral position, in which the flat plane of the reflector is set at an angle to both the axis of the bore first segment 21A and the second bore segment 21B which directs the images from the surgical field, along a viewing channel parallel to retractor blades, to the imaging sensor.

The lens assembly 15 may be disposed within a lens assembly housing 31 with external threads 32, and a portion of the camera housing may be provided in the form of a focus knob 33, rotatably disposed over the posts 25 which capture the reflector mount. The focus knob includes internal threads 34 which engage the external threads of the lens assembly housing 31, such that rotation of the focus knob causes translation of the lens assembly along the imaging sensor imaging axis. (The posts extend through the focus knob and into notches 35 in the lens assembly housing 31 to prevent rotation of the lens assembly housing. An additional post 36 may extend from the bearing ring 28 and into a notch of the lens assembly, to rotationally lock the lens assembly and/or rotationally lock the bearing ring within the camera assembly.) The housing is closed at the back end by a cap 37. An attachment means 38 for attaching the camera assembly housing to the retractor is fixed to the camera assembly at a convenient point, and in a configuration keyed to a receiving component on the retractor with which it will be used. The attachment means 38 may also be secured to this front housing, or secured elsewhere on the camera assembly.

Figure 8:
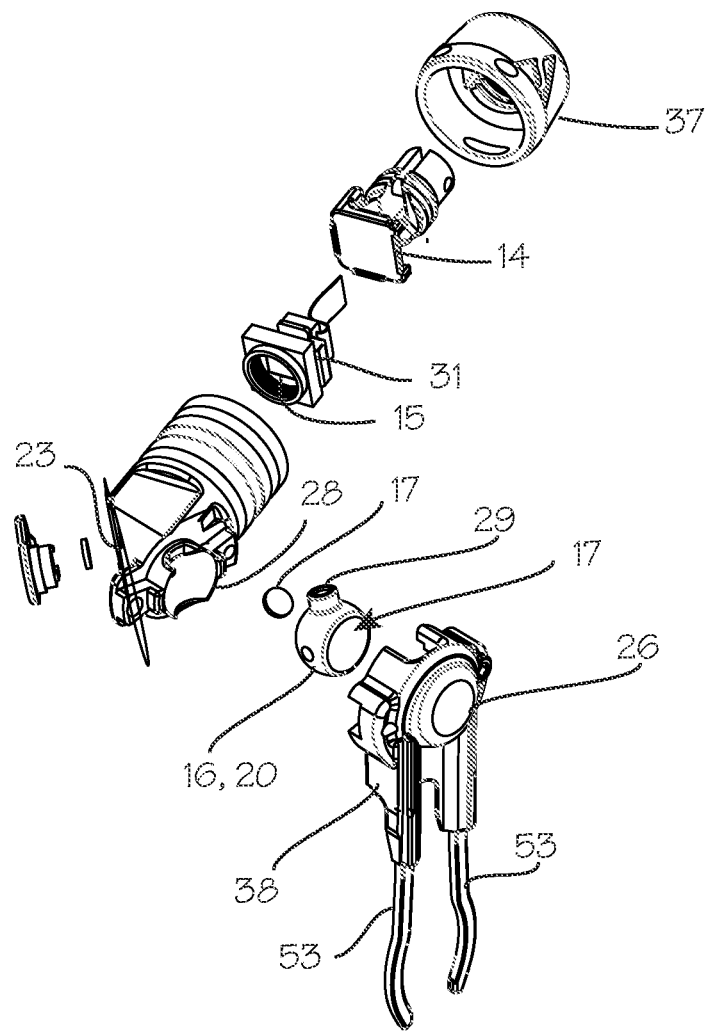
FIG. 8 is an exploded view of the camera assembly according to FIG. 6.

FIG. 8 illustrates an embodiment of the camera assembly with a camera image sensor disposed at an angle from the axis of the mirror and rotating ball, described in FIG. 6, with various optional components which support the rotatable mirror. This Figure includes the reflector 17, reflector mount spherical body 16, 20, the imaging sensor 14, the lens assembly 15 within a lens assembly housing 31 illustrated in FIG. 7. The camera image sensor in this configuration is not in-line with the reflector 17, or the bore 21 of the reflector mount spherical body 16, 20, but the camera assembly includes the additional reflector 23 in the optical path between the first reflector 17 and the imaging sensor 14, positioned to reflect light from the first reflector 17 to the imaging sensor 14.

Other components shown in FIG. 8 include the end cap 37, the front housing 26, and the camera-to-retractor attachment means 38. The camera-to-retractor attachment means 38, shown also in FIG. 12, is secured to the front housing, as in FIG. 7. The post 29 is, as in FIG. 7, limited in extent such that it does not extend beyond the housing. The bearing ring 28, as in FIG. 7, is configured to securely capture the reflector mount between the bearing ring and front housing. In FIG. 8, the pocket in the bearing ring with a spherical surface configured to rotationally support the spherical body is visible. This configuration omits the posts 25 of FIG. 7, and a pocket with a spherical surface, in the inside of the front housing 26 provides additional inner spherical support for the spherical body.

Though FIG. 8 illustrates a configuration with the camera sensor imaging axis set perpendicular to the reflector reflection axis, the camera may be located and oriented such the camera sensor imaging axis is set at various angles to the reflector reflection axis, to accommodate placement of the camera assembly on retractors of various configuration which may include structures which interfere with a camera assembly with a different reflector reflection axis-to-camera sensor imaging axis angle. The additional reflector 23, as illustrated, is fixed at a 45° angle to the reflector reflection axis, but may be rotatably fixed relative to the first reflector 17, and non-rotatable fixed relative to the camera sensor imaging axis. The bearing ring, additional reflector, lens assembly and lens assembly housing and imaging sensor may be dispose, as shown, generally in a plane perpendicular to the camera assembly viewing axis and working channel, or they may be set at other angles, such as parallel to, and offset from, the camera assembly viewing axis and working channel.

Figure 9:
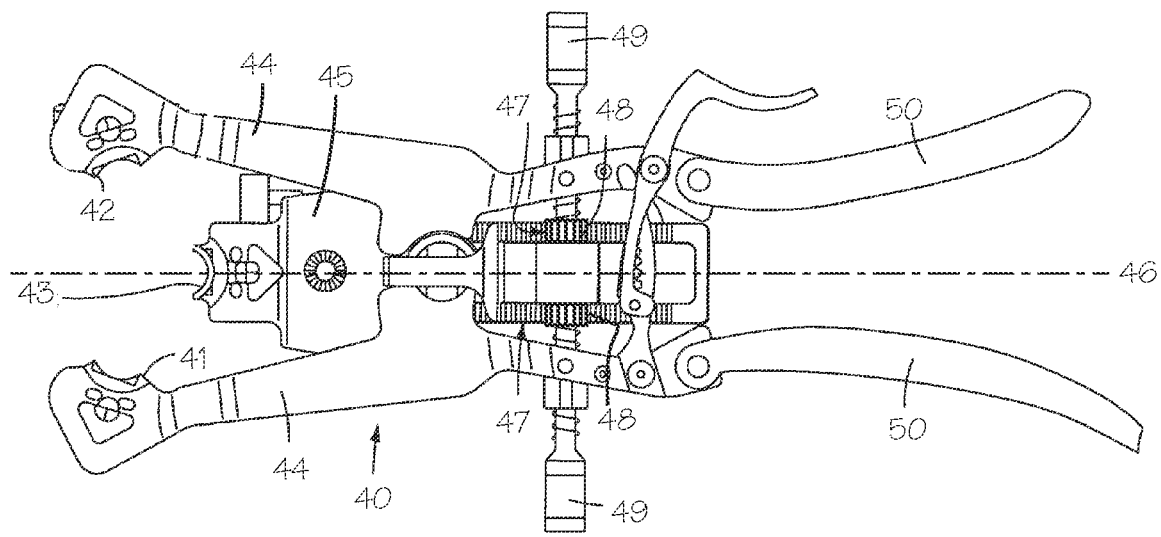
Figure 10:
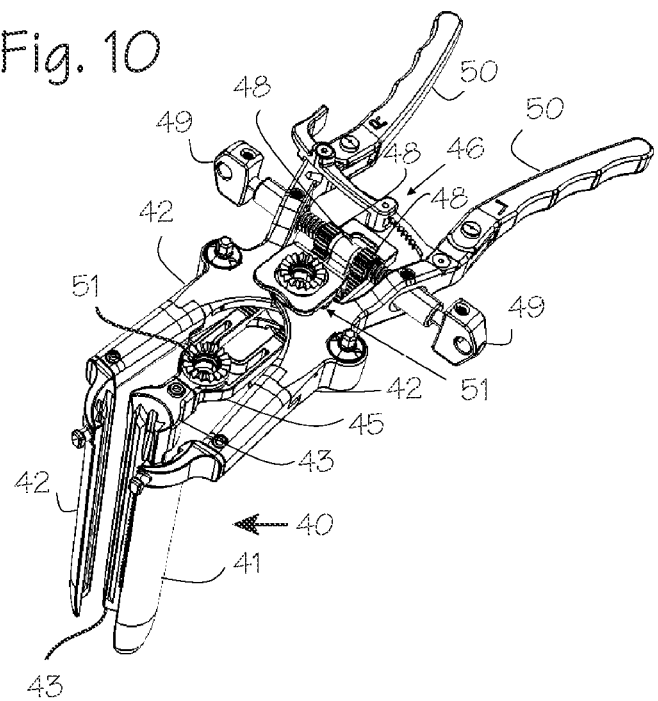

FIGS. 9, 10 and 11 illustrate a typical retractor with which the camera assembly of FIGS. 2, 3 and 7 may be used. This retractor comprises a plurality of partial-pipe blades. FIG. 9 shows a top view of a split tube retractor 40 which includes three blades 41, 42 and 43, with two blades 41 and 42 mounted on blade support arms 44, and one blade 43 mounted on translation member 45. The blade 43 (the central blade) is fixed to the translation member, which in turn is translatable along the horizontal long axis 46 of the retractor through rack and pinion arrangement (rack 47 secured to the translating member and pinion 48 rotatable through knobs 49). The two blades 41 and 42 may be moved toward and away from each other through operation of the handles 50 to enlarge the working channel defined by the blades. A similar retractor is shown in a perspective view in FIG. 10, and the blades are shown in FIG. 11. The retractors include ratcheted table-lock mounting features (one or more locking joints) 51, intended to be secured to table locking arms which serve to secure the retractor in place during surgery. The camera assembly may be configured with a threaded mounting feature with matching teeth, so that the camera assembly may be mounted to the retractor using the pre-existing table-lock mounting feature 51 on extant retractors, on the proximal end of any one of the retractor blades 41, 42 or 43, or on one of the arms 44.

FIG. 11 is a perspective view of the retractor blades 41, 42 or 43 of the retractors shown in FIGS. 9 and 10, showing the inner surface of the blades (the surface facing the working channel). The inner surface may include longitudinal grooves 52 on either side of the blade, or a single channel running down the blade (typically provided to accommodate light wands). An attachment means 38 suited for use with the retractor blades of FIGS. 9, 10 and 11 is shown in FIG. 12. The camera assembly portion housing the mirror mounting structure is attached, releasably or non-releasably, to an expandable clip 53 (preferably biased to an expanded configuration, and compressible to fit the tines into the grooves 52 and thereafter expand in the grooves to securely hold the camera assembly in place, and may be elastically expandable, or spring biased).

Figure 13:
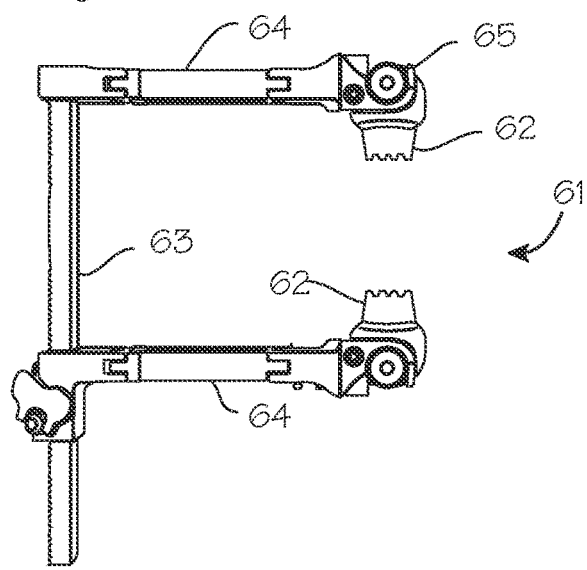
FIGS. 13, 14 and 15 illustrate a McCulloch retractor in combination with the camera assembly of FIGS. 2, 3 and 7.
Figure 14:
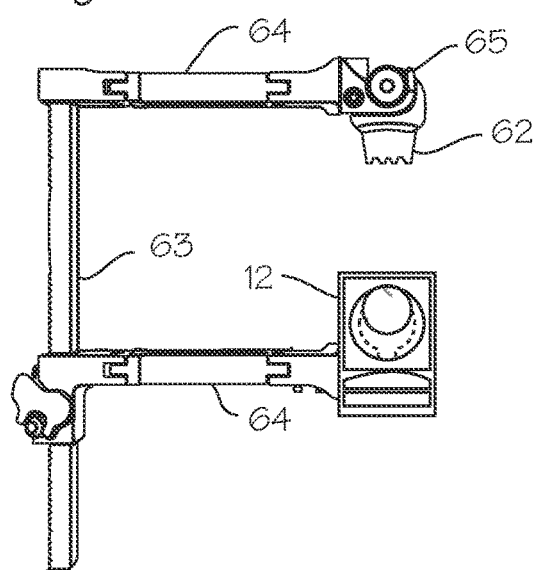
Figure 15:
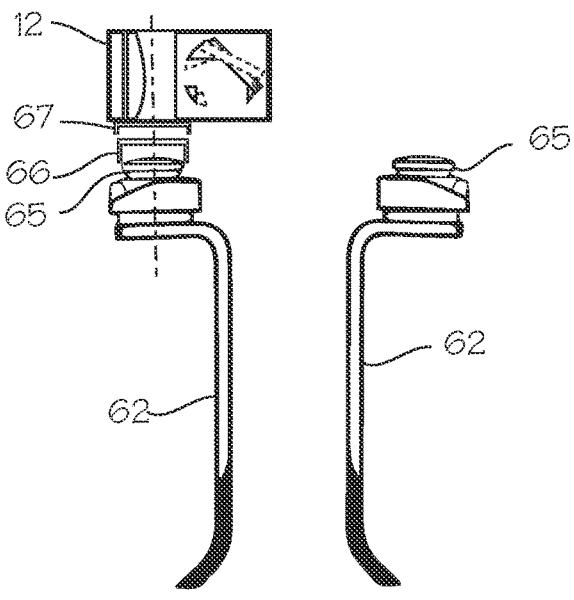

The previous figures illustrate use of the camera assembly with a split tube retractor. The camera assembly may be used with a single blade retractor such as a Caspar blade retractor or other multi-blade retractor system such as a McCulloch retractor system, illustrated in FIGS. 13 and 14. The McCulloch retractor 61 comprises a plurality of retractor blades 62 (flat blades in this depiction) defining the working channel. The flat blades are secured to a frame comprising ratcheted frame members 63 and blade support arms 64 with fixation features comprising bolt heads 65. As with the split tube retractors, the blades establish a working channel with a proximal end corresponding to proximal ends of the blades and a distal end corresponding to distal ends of the blades, where the distal end of each blade is configured for insertion into the body of the patient to establish the working channel. As shown in FIGS. 14 and 15, the camera assembly may be fixed to the proximal end of one of the blades, via releasable connection to a blade fixation element or one of the frame members of the McCulloch retractor, such that the reflector viewing axis is directed toward the distal end of the working channel, and the post is operable to rotate the rotatable element to change the angle of the viewing angle relative to the long axis of the working channel. FIG. 15 shows a side view of the McColloch blade 62 and camera assembly 12. The first annular snap ring 66 is an example of a camera-to-retractor "attachment means" which serves to releasably attach the camera assembly to the retractor. The second annular snap ring 67 serves as a first component of a "connector means" for connecting the camera assembly to the camera-to-retractor "attachment means" 66 (a "camera to 'retractor attachment means'" connector means) while the upper surface of the camera-to-retractor "attachment means" 66, is configured with an annular detent sized to mate with the annular snap ring 67, and constitutes a second component of the connector means. When the system is provided in kit form with various other camera-to-retractor "attachment means" 66 configured for releasable attachment to other features of the frame members, the surgeon may readily remove the snap ring camera-to-retractor "attachment means" 66 from the "connector means" 67 and secure another form of camera-to-retractor "attachment means" 66 to the "connector means" 67. The annular snap ring configuration may be replaced with any readily assembled releasable or non-releasable connector means.

A variety of attachment means 38 may be provided, in a kit with the camera assembly, with each attachment means configured for securing the camera assembly to retracting with different features for mating the two components. The two downwardly depending fingers that serve as attachment means in FIG. 7, or the expandable clip that serves as attachment means in FIG. 12, a single downwardly depending blade for other retractors, or a peg matching the shape of any aperture in the retractor, such as aperture 68 in FIG. 9, or the snap ring 66 in FIG. 15, or clamps, or rack and pinion fittings, may serve as attachment means. Each of these camera-to-retractor "attachment means" may be provided in configuration with a connector means, as described above, that can be fixed to the camera assembly by a surgeon, and provided to surgeons in a kit including the camera assembly and a variety of camera-to-retractor "attachment means", so that the surgeon, having selected a proper retractor for a surgery, can choose a corresponding camera-to-retractor "attachment means" which matches available features on the retractor, and secure the corresponding attachment means to the camera assembly, and then secure the combined camera assembly and attachments means the retractor.

Thus, the camera assembly of any embodiment described above can be provided in a kit including
 a first camera-to-retractor attachment means configured to secure to the camera assembly to the first fixation feature
 at least a second camera-to-retractor attachment means configured to secure to the camera assembly to the second fixation feature;
 and including a camera assembly and attachment means with matching first and second components of a readily attachable (preferably releasably attachable) connector means, such that
  the camera assembly comprises a first component of a "connector means" for connecting the camera assembly to both camera-to-retractor "attachment means" and
  each camera-to-retractor "attachment means" comprises a second component of a "connector means" for connecting the camera assembly to both camera-to-retractor "attachment means", said second component configured to mate with the first component.

Any number of additional camera-to-retractor "attachment means", configured to match various fixation features on various commercially available retractors, may be include in the kit.

Any readily assembled "connector means" for connecting the camera assembly to the camera-to-retractor "attachment means" may be used as a releasable attachment means, including snap joint, such as cantilever snap joints with paired cantilever beams and lugs on one component and matching retaining lip on the other, torsion snap joints, annular snap joints, paired toe-clip style connector components, RCA-type connector components, bayonet fitting components, spade style connector components, quick disconnect coupling components (with one element of each connector system on the camera assembly, and one on the camera-to-retractor attachment means), threaded couplings, cam lock fitting, or a braking clamp mechanism for the camera to mount on the edge of a blade and can travel toward the surgical site (below tissue) and locked at various depths. The mirror may be rotated such that the camera assembly is vertical relative to the distal optical element. The camera-to-"retractor attachment means" may be releasably attachable, meaning that they can be assembled and disassembled without the use of tools, and without damaging components of either side of the coupling (to the point of making them unusable for re-attachment), so that a surgeon can select a camera-to-retractor attachment means to suit any retractor chosen for a surgery, and attach the camera assembly to the camera-to-retractor attachment means, while retaining the option to remove the camera-to-retractor attachment means from the camera assembly and attach a different camera-to-retractor attachment means so that the camera assembly can be fixed to a different feature on the retractor, or to a different retractor, as required by the exigencies of a particular operation.

The camera assembly is illustrated in relation to retractors, but are equally useful with distractors, which, for the purposes of this application may be considered to be retractors with additional features for attachment to bones so that they can be used to force bones apart (for example, moving vertebrae apart). The camera assembly is also illustrated in relation to retractors primarily suitable for spinal surgery, but are equally useful with retractors for any surgery.

The camera assembly may overhang the working channel, with the distal-most optical component of the system suspended above (proximal to) and projecting out slightly over the working channel, or with the entirety of the camera assembly above (proximal to) the working channel and the proximal ends of the retractor elements. The camera assembly may instead be positioned within the working channel, along the blade of a single-blade retractor or along one of the blades of a multi-blade retractor.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

We claim:

1. A camera and retractor system for access to a surgical target site within a body of a patient, said system comprising:
   a retractor system comprising at least one retracting element operable to retract body tissue to create a surgical working channel defined by said retracting element of the retractor system for access to the surgical target site within the body of the patient;
   a camera assembly secured to the retractor system at the proximal end of the working channel, with a portion of the camera assembly overhanging the working channel and extending into a space defined by the working channel; wherein
   the camera assembly is characterized by a viewing axis and comprises an image sensor with an image sensor axis, a first reflecting element positioned to reflect light from the working channel, to the image sensor; and
   the camera assembly further comprises a rotatable reflector mount, rotatable relative to the image sensor and disposed within the camera assembly and configured to rotate the first reflecting element relative to the image sensor to direct images from the surgical working channel to the image sensor.

2. The camera and retractor system of claim 1 wherein:
   the rotatable reflector mount is disposed between the image sensor and the first reflecting element, with a first optically transmissive portion disposed between the image sensor and the first reflecting element, and with said first reflecting element fixed to the rotatable reflector mount.

3. The camera and retractor system of claim 2 wherein:
   the first optically transmissive portion comprises a bore passing through the rotatable reflector mount.

4. The camera and retractor system of claim 1 wherein:
   the rotatable reflector mount comprises a second optically transmissive portion disposed between the reflecting element and the surgical working channel.

5. The camera and retractor system of claim 1 wherein:
   the rotatable reflector mount comprises a truncated spherical body, with a first bore segment aligned with the viewing axis and a second bore segment aligned with the image sensor axis.

6. The camera and retractor system of claim 1 wherein:
   the rotatable reflector mount includes a socket, accessible from the exterior of the camera assembly, configured to accept an element whereby a user may manipulate the rotatable reflector mount.

7. The camera and retractor system of claim 1 further comprising:
   a post fixed to the rotatable reflector mount, extending from the rotatable reflector mount, for rotating the rotatable reflector mount, whereby the viewing axis may be altered within the working channel.

8. The camera and retractor system of claim 1 wherein:
   the camera assembly has a distal-most optical surface, and said distal-most optical surface is disposed proximate the proximal end of the retracting element.

9. The camera and retractor system of claim 1 wherein:
   the at least one retracting element comprises a tubular retractor comprising a tube with a long axis, a proximal end and a distal end, said distal end configured for insertion into the body of the patient, said tube having a lumen constituting the surgical working channel; and wherein
   the camera assembly is non-rotatably fixed to the proximal end of the tube, the viewing axis is directed toward the distal end of the tube, and the rotatable reflector mount is operable to change the angle of the viewing angle relative to the long axis of the tube.

10. The camera and retractor system of claim 9 wherein:
    the tubular retractor comprises a split tube retractor, having a plurality of partial-pipe blades; and
    the camera assembly is fixed to one of the partial-pipe blades.

11. The camera and retractor system of claim 1 wherein:
    the at least one retracting element comprises a single blade; and
    the camera assembly is fixed to the proximal end of the single blade.

12. The camera and retractor system of claim 1 wherein:
    the camera assembly is fixed to the retractor via a mounting feature on the retractor.

13. The camera and retractor system of claim 1 wherein:
    the retractor system comprises a McCulloch retractor, the at least one retracting element comprising a plurality of blades, said blades defining the working channel with a proximal end corresponding to proximal ends of said blades and a distal end corresponding to distal ends of said blades, said distal end configured for insertion into the body of the patient to establish the working channel in the body of the patient, said working channel having a longitudinal axis extending from the surgical site near the distal end of the blades to an opening at the proximal end of the blades, said blades fixed to a frame; and wherein
    the camera assembly is fixed to the proximal end of one of the blades or the frame, such that the viewing axis is directed toward the distal end of the working channel, and a post is operable to rotate the rotatable reflector mount to change the angle of the viewing axis relative to the long axis of the working channel.

14. The camera and retractor system of claim 1, further comprising:
    releasable attachment means for releasably attaching the camera assembly to the retracting element.

15. The camera and retractor system of claim 14 wherein the image sensor is disposed with an imaging axis parallel to, but offset from, the reflector viewing axis, and/or the central viewing axis of the camera assembly, said system further comprising:
    a third reflector element operable to redirect light from the second reflector toward the image sensor.

16. The camera and retractor system of claim 1 wherein the first reflecting element is characterized by a first reflecting element reflecting axis and the image sensor is characterized by an imaging axis offset from the reflector reflection axis, said system further comprising:
    a second reflector element operable to redirect light from the first reflecting element along said imaging axis offset from the reflector reflection axis.

17. A camera assembly kit for use with
    a first retractor system comprising a first retracting element, said first retractor element having a distal end configured for insertion into a body of a patient to create a surgical working channel, said first retractor system comprising a first fixation feature,
    a second retractor system comprising a second retracting element, said second retractor element having a distal end configured for insertion into a body of a patient to create a surgical working channel, said second retractor system comprising a second fixation feature, said camera assembly kit comprising:

a camera assembly is characterized by a viewing axis and comprises an image sensor with an image sensor axis, a first reflecting element positioned to reflect light from the working channel, to the image sensor; and a rotatable reflector mount disposed within the camera assembly and configured to rotate the first reflecting element to direct images from the viewing axis to the image sensor;

a first camera-to-retractor attachment means configured to secure to the camera assembly to the first fixation feature; and at least a second camera-to-retractor attachment means configured to secure to the camera assembly to the second fixation feature;

wherein:

the camera assembly comprises a first component of a connector means for connecting the camera assembly to both the first and second camera-to-retractor attachment means and each of the first and the second camera-to-retractor attachment means comprises a second component of a connector means for connecting the camera assembly to both the first and second camera-to-retractor attachment means, said second component configured to mate with the first component.

18. The camera assembly kit of claim 17 wherein:
the rotatable reflector mount is disposed between the image sensor and the first reflecting element, with a first optically transmissive portion disposed between the image sensor and the first reflecting element, and with said first reflecting element fixed to the rotatable reflector mount.

19. The camera assembly kit of claim 17 wherein:
the rotatable reflector mount comprises a second optically transmissive portion disposed between the reflecting element and the surgical working channel.

20. The camera assembly kit of claim 17 wherein:
the rotatable reflector mount comprises a truncated spherical body, with a first bore segment aligned with the viewing axis and a second bore segment aligned with the image sensor axis.

21. The camera assembly kit of claim 17, wherein:
the first optically transmissive portion comprises a bore passing through the rotatable reflector mount.

22. The camera assembly kit of claim 17 wherein:
the rotatable reflector mount includes a socket, accessible from the exterior of the camera assembly, configured to accept an element whereby a user may manipulate the rotatable reflector mount.

23. The camera assembly kit of claim 17 wherein:
a post fixed to the rotatable reflector mount, extending from the rotatable reflector mount, for rotating the rotatable reflector mount, whereby the viewing axis may be altered within the working channel.

24. The camera assembly kit of claim 17 wherein the first reflecting element is characterized by a first reflecting element reflecting axis and the image sensor is characterized by an imaging axis offset from the reflector reflection axis, said system further comprising:
a second reflector element operable to redirect light from the first reflecting element along said imaging axis offset from the reflector reflection axis.

25. The camera assembly kit of claim 24 wherein the image sensor is disposed with an imaging axis parallel to, but offset from, the reflector viewing axis, and/or the central viewing axis of the camera assembly, said system further comprising:
a third reflector element operable to redirect light from the second reflector toward the image sensor.

* * * * *